United States Patent [19] [11] 4,110,452
Rovnyak et al. [45] Aug. 29, 1978

[54] PYRAZOLO (1,5-C) QUINAZOLINE DERIVATIVES AND RELATED COMPOUNDS

[75] Inventors: George C. Rovnyak, Hopewell, N.J.; B. Richard Vogt, Yardley, Pa.

[73] Assignee: E. R. Squibb & Sons, Inc., Princeton, N.J.

[21] Appl. No.: 842,776

[22] Filed: Oct. 17, 1977

[51] Int. Cl.² ............... C07D 487/04; A61K 31/415; A61K 31/505
[52] U.S. Cl. ............................. 424/251; 544/252
[58] Field of Search ............ 260/256.4 F; 424/251

[56] References Cited
U.S. PATENT DOCUMENTS

| 3,171,740 | 3/1965 | Menzel et al. | 260/256.4 F |
| 3,313,815 | 4/1967 | Wolfe et al. | 260/256.4 F |
| 3,531,482 | 9/1970 | Ott | 260/256.4 F |

Primary Examiner—Donald G. Daus
Assistant Examiner—James H. Turnipseed
Attorney, Agent, or Firm—Lawrence S. Levinson; Merle J. Smith; Burton Rodney

[57] ABSTRACT

Compounds are provided having the structure

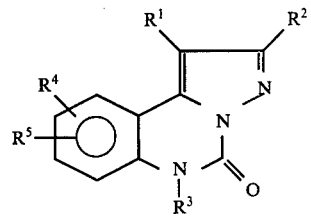

wherein $R^1$ is alkylamino, dialkylamino, or

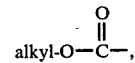

wherein alkyl in the above groups contains 1 to 4 carbons; $R^2$ is alkylamino, dialkylamino or

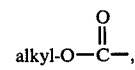

wherein alkyl in the above groups contains 1 to 4 carbons; at least one of $R^1$ and $R^2$ being alkylamino or dialkylamino; $R^3$ is hydrogen, lower alkyl, benzyl or phenyl (optionally substituted with $R^8$), or

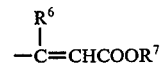

(wherein $R^6$ is amino, alkylamino or dialkylamino, and $R^7$ is alkyl); and $R^4$, $R^5$ and $R^8$ are the same or different and represent hydrogen, lower alkyl, lower alkoxy, alkanoyloxy, benzyloxy, hydroxy, halogen (Cl, Br and F), nitro and trifluoromethyl.

13 Claims, No Drawings

PYRAZOLO (1,5-C) QUINAZOLINE DERIVATIVES AND RELATED COMPOUNDS

The present invention relates to pyrazolo[1,5-c]-quinazoline derivatives of the structure

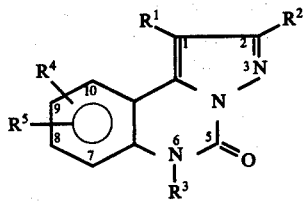

wherein
$R^1$ is alkylamino, dialkylamino, or

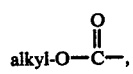

wherein alkyl in the above groups contains 1 to 4 carbons; $R^2$ is alkylamino, dialkylamino or

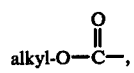

wherein alkyl in the above groups contains 1 to 4 carbons; with the proviso that at least one of $R^1$ or $R^2$ is alkylamino or dialkylamino;
$R^3$ is hydrogen, lower alkyl, benzyl or phenyl (optionally substituted by an $R^8$ radical as defined below),

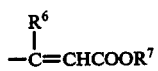

(wherein $R^6$ is amino, alkylamino or dialkylamino, and $R^7$ is alkyl),
$R^4$, $R^5$ and $R^8$ may be the same or different and are hydrogen, lower alkyl (1-4 carbons), lower alkoxy (1-4 carbons), hydroxy, alkanoyloxy (2-5 carbons),

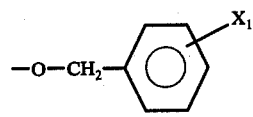

($X_1$ is hydrogen, lower alkoxy (1-4 carbons)), hydroxy, Cl, F, Br, $CF_3$ or $NO_2$.

Unless otherwise indicated the term "lower alkyl" or "alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated, the term "lower alkoxy" or "alkoxy" includes straight and branched chain radicals which correspond to the above lower alkyl groups attached to an oxygen atom.

Unless otherwise indicated, the term "lower alkanoyl" or "alkanoyl" as employed herein includes any of the above lower alkyl groups linked to a carbonyl group.

Unless otherwise indicated, the term "aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like), di(-lower alkyl)phenyl (e.g., 2,4-dimethylphenyl, 3,5-diethylphenyl, and the like), halophenyl, (e.g., chlorophenyl, bromophenyl, iodophenyl, fluorophenyl).

Preferred compounds encompassed by the structure of formula I include, but are not limited to, the following:

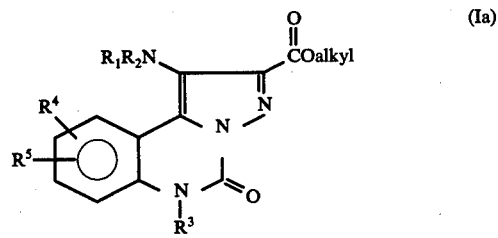

(wherein $R_1$ and/or $R_2$ is H or alkyl, at least one of $R_1$ and $R_2$ being alkyl, and $R^3$ is H, lower alkyl, benzyl, phenyl,

wherein $R^6$ is amino, alkylamino or dialkylamino and $R^7$ is alkyl)

More preferred are compounds of formula Ia wherein $R^4$ and $R^5$ are hydrogen.

The compounds of Formula I of the invention may be prepared by several methods.

One such method involves the preparation of compounds of the structure

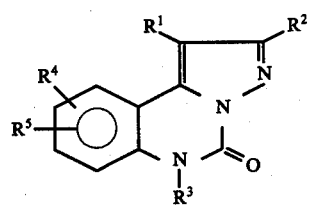

wherein $R^1$ to $R^5$ are as defined hereinbefore. This method (hereinafter called the "first method") involves reacting a substituted acetylene of formula III with a 3-diazoindol-2(3H)one of formula II in accordance with the following reaction scheme:

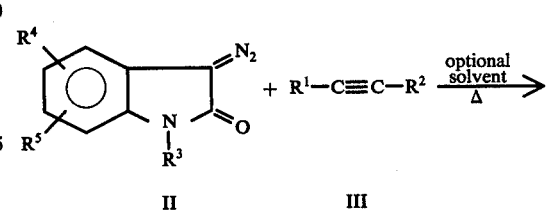

-continued

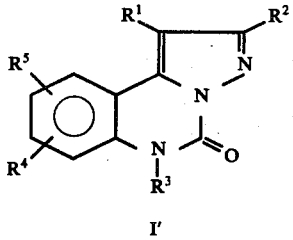

I'

The reaction can be carried out in an excess of the acetylenic compound or in an optional solvent which is essentially inert to both of the reactants. Examples of suitable optional solvents include, among others, aliphatic hydrocarbons, such as pentane, hexane, octane, and the like; aromatic hydrocarbons, such as benzene, toluene, the xylenes, and the like; halogenated hydrocarbons, such as methylene chloride, chloroform, carbon tetrachloride, ethylene dichloride, chlorobenzene, bromobenzene, and the like; ethers, such as diethyl ether, diisopropyl ether, methyl butyl ether, tetrahydrofuran, 1,4-dioxane and the like; aliphatic esters, such as methyl acetate, ethyl acetate, butyl acetate and the like; and miscellaneous solvents, such as N,N-dimethylacetamide, dimethyl sulfoxide, and the like. The aromatic hydrocarbons, such as benzene and toluene and the chlorinated hydrocarbons, such as methylene chloride are preferred. The amount of solvent employed is not critical, but should be sufficient to permit adequate agitation. Typically, the weight-to-volume ratio of reactants to solvent is at least about 1:2 and preferably at least about 1:3, although larger volumes of solvent can be employed if desired. The molar ratio of substituted acetylene to 3-diazoindol-2(3H)-one can vary from about 1:1 to about 100:1. Preferably, the molar ratio will be in the range of from about 1:1 to about 40:1. Reaction time, while to some extent temperaturedependent, can vary from about 15 minutes to about 48 hours. Preferably, the reaction time will be in the range of from about 15 minutes to about 30 hours. The reaction is normally carried out at an elevated temperature, i.e., from about 40° to about 150° C., conveniently at the reflux temperature of the solvent, if used, or below about 150° C. A reaction temperature of from about 70° to about 120° C. is preferred. Isolation of the compounds of formula I is accomplished by standard procedures. With the preferred optional solvents, the pyrazolo[1,5-c]quinazolin-5(6H)-one is relatively insoluble at ambient temperature or lower, and isolation of the reaction product is accomplished by cooling the reaction mixture and removing the precipitate.

In the absence of solvent, the remaining excess substituted acetylene can be optionally removed by distillation in vacuo; the product is isolated by triturating the distillation residue with a preferred solvent followed by filtration of the precipitated product. If desired, the pyrazolo[1,5-c]quinazolin-5(6H)-one can be recrystallized from additional reaction solvent.

The substituted acetylene preferably reacts with the 3-diazoindol-2(3H)-one to give a pyrazolo[1,5-c]quinazolin-5(6H)-one having $R^1$ in the 1-position. However, reverse addition can occur which results in $R^2$ being in the 1-position. Such reverse addition is not favored, and when $R^1$ is hydrogen or lower alkoxycarbonyl, little if any reverse addition product is formed. The presence of reverse addition compound is not detrimental to the isolation and purification of the desired product. However when $R^1$ is $C_1$-$C_4$ alkyl, phenyl, or monosubstituted phenyl, the amount of reverse addition product which is formed increases with increasing bulk of $R^1$.

The substituted acetylenes employed in the above-described process in general are commercially available or readily prepared by well-known procedures.

The 3-diazoindol-2(3H)-ones employed in the above-described processes in general are prepared from the corresponding isatin compound. The preparation of isatin compounds is well known in the art. The required N-substituted isatin is obtained by either of two routes, depending upon whether the N-substituent is attached by an (1) alkyl or aralkyl carbon atom or (2) aryl carbon atom. When the desired isatin nitrogen substituent is attached by an alkyl or aralkyl carbon atom, the isatin compound is prepared by N-alkylation of the present compound with an alkyl or aralkyl halide or by an unsaturated conjugated ester, such as a substituted propiolate ester in the optional presence of a strong base such as, for example, sodium hydride. However, when an aryl substituent on the isatin nitrogen is desired, a different procedure must be employed. In that case, the desired N-aryl isatin is prepared directly by cyclization with oxalyl chloride of an appropriatelysubstituted diarylamine.

Once the desired isatin has been obtained, the corresponding 3-diazoindol-2(3H)-one is prepared in accordance with known procedures. See, for example, J. M. Michowski, Tetrahedron Letters, 1773 (1967) and M. P. Cava, et al., J. Am. Chem. Soc., 80, 2257 (1958). The appropriate isatin compound is treated with p-toluenesulfonylhydrazine. The resulting hydrazone then is treated with a base such as aqueous sodium hydroxide or aluminum oxide to give the desired 3-diazoindol-2(3H)-one.

Compounds of formula I wherein $R^4$ and/or $R^5$ are OH are prepared by reacting compounds of formula I, wherein $R^4$ and/or $R^5$ are

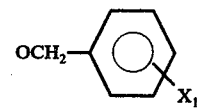

with an appropriate reducing agent under selective conditions in an inert organic solvent.

Typical reducing agents include a metal catalyst, preferably Raney nickel, and hydrogen in the optional presence of a hydrogen halide in an inert organic solvent. Typical solvents include alkanols of 1-6 carbons such as methanol, ethanol and the like. The preferred optional hydrogen halides are hydrogen chloride and hydrogen bromide. The reactions are carried out for from about 1/6 hour to about 92 hours, preferably for from about ½ to about 24 hours to from about −20° to about 100° C.

The last-mentioned compounds of formula I can also be prepared by reacting the last-mentioned starting materials of formula I with at least about 0.5, preferably at least about 0.8, molar equivalents of an inorganic hydrogen halide (preferably hydrogen chloride, hydrogen bromide or hydrogen fluoride) or with a halogenated alkyl carboxylic acid of 1-4 carbons, preferably trifluoroacetic acid. The reaction is run in anhydrous hydrogen fluoride, or, when employing other acids, in an optional inert solvent.

Typical solvents include alkyl carboxylic acids of 1-3 carbons, such as acetic acid and the like; ethers such as diethyl ether, dioxane, tetrahydrofuran and the like; alkanols of 1-6 carbons such as methanol, ethanol, and the like; alkyl esters wherein both the acid and the alcohol from which the ester is derived may have from 1-4 carbon atoms such as ethyl acetate, propyl acetate, ethyl propionate and the like; halogenated hydrocarbon such as methylene chloride, chloroform, di-, tri- and tetrachloroethanes and the like; nitroalkanes of 1-4 carbons such as nitromethane, nitroethane and the like; or alkyl ketones having alkyl radicals of 1-4 carbons such as acetone, methylethyl ketone and the like.

The reaction is carried out at from about −50° C. to about 200° C., preferably from about 0° C. to about 120° C., until a significant amount of end product is obtained, typically, for from about 1/10 to about 92, preferably from about 1/6 to about 30 hours. The product is isolated by conventional techniques. For example, with all acids except hydrogen fluoride, the reaction mixture is diluted with an inert water-immiscible organic solvent, washed with dilute aqueous sodium bicarbonate, dried and chromatographed. When using hydrogen fluoride, the hydrogen fluoride is evaporated, the residue dissolved in an inert organic solvent, such as halogenated hydrocarbons, e.g., methylene chloride, chloroform or trichloroethylene; alkyl esters wherein both the acid and the alcohol from which the ester is derived may have from 1-4 carbon atoms, e.g., ethyl acetate, propyl acetate, ethyl propionate and the like, washed with water, dried and chromatographed.

Compounds of formula I wherein $R^4$ and/or $R^5$ are lower alkoxy are also prepared by reacting compounds of formula I wherein $R^4$ and/or $R^5$ are hydroxyl and where $R^3 \neq H$ or, if $R^3 = H$ the product may have $R^3 =$ lower alkyl group of $R^4$ and/or $R^5$, with from about 0.5 to about 12, preferably from about 0.8 to about 3.0 molar equivalents of an appropriate base, e.g., $KHCO_3$, followed by reaction of the thus formed salt with a corresponding molar equivalent of an appropriate alkylating agent of formula lower alkyl-M wherein M is any group which is compatible with lower alkyl (1-4 carbons), and capable of being displaced by aryloxide anion under the reaction conditions. Some typical M groups include halogen, preferably chlorine, bromine, iodine;

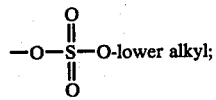

or an alkyl or arylsulfonate of formula

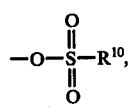

wherein $R^{10}$ can be alkyl of 1-6 carbons or aryl of from about 6 to 10 carbons optionally substituted by halogen, nitro or alkyl of 1-3 carbons. The reaction is run in an essentially inert organic solvent, e.g., lower alkyl ketones, such as methyl ethyl ketone.

Other typical bases include alkali metals (preferably lithium, sodium and potassium) and their salts of alkanols of 1-6 carbons such as methanol, ethanol, i-propanol, t-butyl alcohol, n-amyl alcohol and the like; of ammonia; of mono- and dialkylamines wherein the alkyl groups contain from 1-6 carbons such as ethylamine, diethylamine, di-isopropylamine, cyclohexyl isopropylamine and the like; of acidic hydrocarbons such as triphenylmethane and the like; thallous salts of the preceding alkanols, alkali metal (preferably sodium) hydrides.

Other typical organic solvents include alkanols of 1-5 carbons such as methanol, ethanol, t-butyl alcohol, n-butanol and the like; ethers of 4– carbons such as tetrahydrofuran, dioxane, diphenyl ether, 1,2-dimethoxyethane and the like; N,N-dialkylformamides, N,N-dialkylalkanoylamides wherein the alkyl and alkanoyl radicals have 1-4 carbons, such as dimethylformamide, dimethylacetamide and the like; dialkyl sulfoxides of 3-5 carbons such as dimethylsulfoxide and the like; hexamethylphosphorous triamide.

The reaction is carried out at from about −20° to about 300° C., preferably from about 0° to about 100° C. for from about 0.2 hour to about 96 hours, preferably from about 0.5 hour to about 72 hours.

The products are isolated by conventional techniques. For example, the reaction mixture is refluxed for 5 hours, cooled, adjusted to pH 6 with aqueous HCl and evaporated; the residue is diluted with a water-immiscible, inert solvent such as methylene chloride, washed with water, dried and chromatographed.

In the above reaction when $R^3 = H$ in the starting material, the resultant product may have $R^3 =$ lower alkyl, depending on the strength of the base used and on the relative amount of alkylating agent employed in the reaction.

Compounds of formula I wherein $R^4$ and $R^5$ are other than OH and $R^3$ is other than hydrogen or optionally substituted phenyl are also prepared by reacting compound of formula I wherein $R^3$ is hydrogen with from about 0.5 to about 2, preferably from about 0.8 to about 1.3 molar equivalents of an appropriate base, followed by reaction of the thus formed salt with a corresponding molar equivalent of an appropriate alkylating agent of formula $R^3$-M wherein $R^3$ is other than hydrogen or optionally substituted phenyl and M is any group which is compatible with $R^3$ and capable of being displaced by the salt under the reaction conditions. Some typical M groups include halogen, preferably chlorine, bromine, iodine;

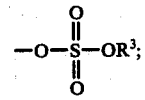

or an alkyl or arylsulfonate of formula

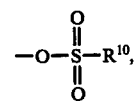

where $R^{10}$ can be alkyl of 1-6 carbons or aryl of from about 6 to 10 carbons optionally substituted by halogen, nitro or alkyl of 1-3 carbons. The reaction is run in an essentially inert organic solvent.

Typical bases include alkali metals (preferably lithium, sodium and potassium) and their salts of alkanols of 1-6 carbons such as methanol, ethanol, i-propanol, t- butyl alcohol, n-amyl alcohol and the like; of ammonia; of mono- and dialkylamines wherein the alkyl groups contain from 1-6 carbons such as ethylamine, diethylamine, di-isopropylamine, cyclohexyl isopropylamine and the like; of acidic hydrocarbons such as triphenylmethane and the like; thallous salts of the preceding alkanols, and, preferably, alkali metal hydrides such as sodium hydride.

Typical organic solvents include alkanols of 1-5 carbons such as methanol, ethanol, t-butyl alcohol, n-butanol and the like; ethers of 4-12 carbons such as tetrahydrofuran, dioxane, diphenyl ether, 1,2-dimethoxyethane and the like; N,N-dialkylformamides, N,N-dialkylalkanoylamides wherein the alkyl and alkanoyl radicals have 1-4 carbons, such as dimethylformamide, dimethylacetamide and the like; dialkyl sulfoxides, hexamethylphosphorous triamide and their mixtures.

The reaction is carried out at from about −20° C. to about 300° C., preferably from about 0° C. to about 100° C. for from about 0.2 hour to about 96 hours, preferably from about 0.5 to about 72 hours.

The products are isolated by conventional techniques. For example, the reaction mixture is evaporated; the residue is neutralized with aqueous acid, extracted with a water-immiscible, inert solvent such as methylene chloride, washed with water, dried and chromatographed.

Compounds of the structure

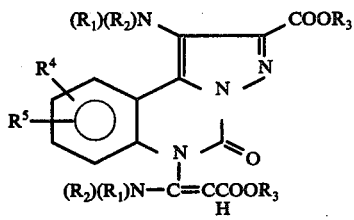

wherein $R_1$, $R_2$ and $R_3$ may be the same or different and are hydrogen or lower alkyl and at least one of $R_1$ or $R_2$ is lower alkyl, may be prepared by reacting a compound of the structure

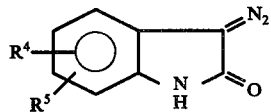

with a yneamine ester of the structure

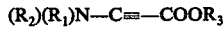  VI in an appropriate solvent such as toluene while heating the reaction mixture at reflux for 5 to 48 hours.

Starting materials or final products that are mixtures of isomers can be separated into the single isomers by methods in themselves known, e.g., by fractional distillation, crystallization and/or chromatography. Racemic products can likewise be resolved into the optical antipodes, for example by separation of diastereomeric salts thereof, e.g., of the fractional crystallization, in the case of basic compounds, of d- or L-tartrates, maleates, -mandelates, -N-acetylphenylalaninates or -camphor sulfonates, or, in the case of acid compounds, d- or L-methylbenzylamine and reconverting the diastereomeric salts into the free antipodes.

Certain of the compounds of formula I may form physiologically acceptable acid-addition salts or base addition salts with inorganic and organic acids or alkali metal or alkaline earth metal bases such as sodium hydroxide or calcium hydroxide. These salts frequently provide useful means for isolating the products from reaction mixtures by forming the salt in a medium in which it is insoluble. The free base may then be obtained by neutralization, e.g., with a base or acid. Then any other salt may again be formed from the free base and the appropriate inorganic acid or base. Illustrative are the hydrohalides, especially the hydrochloride and hydrobromide which are preferred, sulfate, nitrate, phosphate, oxalate, tartrate, maleate, fumarate, citrate, succinate, methanesulfonate, benzenesulfonate, toluenesulfonate, and the like.

The compounds of formula I, and their pharmaceutically acceptable salts, are useful in treating various allergic conditions in mammalian species such as mice, cats, dogs, etc., when administered in amounts ranging from about 1 milligram to about 500 milligrams per kilogram of body weight per day. The compounds can be used prophylactically or therapeutically to treat various allergic and immunological disorders and in particular to treat certain types of asthma, hay-fever, and rhinitis. A preferred dosage regimen would be from about 3 milligrams to about 200 milligrams per kilogram of body weight per day administered in a single dose or plurality of divided doses.

The compounds of formula I, and the pharmaceutically acceptable salts thereof, are anti-allergics which inhibit the effects of certain antigen-antibody reactions and in particular inhibit the release of mediators such as histamine. The anti-allergy activity of these compounds is determined by the reaginic antibody induced passive cutaneous anaphylaxis (PCA) reaction in rats. (See Bach, Immediate Hypersensitivity: Laboratory Models and Experimental Findings, Ann. Rep. Med. Chem., 7: 238-248 (1972), for a discussion of the predictability of clinical efficacy of compounds active in the PCA).

A compound of formula I, or a salt thereof, can be administered by the inhalation of an aerosol or powder as described in U.S. Pat. No. 3,772,336 (i.e., breathing finely divided particles of the active ingredient into the lungs), orally, parenterally. Powders can be prepared by comminuting the active ingredient with a similarly comminuted diluent such as starch or lactose. Suitable forms for oral administration include capsules, tablets, and syrups, and a suitable form for parenteral administration is a sterile injectable. Such unit dosage forms are prepared by compounding with a conventional vehicle, excipients, binders, preservatives, stabilizers, flavoring agents or the like as called for by acceptable pharmaceutical practice. Also, the compounds of this invention can be formulated with other pharmaceutically active compounds such as bronchodilators, steroids, antihistamines, etc.

The compounds of the invention are also useful as antiinflammatory agents as determined by the reverse passive Arthus test [Agents & Actions, 5, 39 (1975)] and are effective in the prevention and inhibition of granuloma formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis.

Furthermore, the compounds of the invention are useful in mammals as inhibitors of 3',5'-cyclic adenosine phosphodiesterase and 3',5'-cyclic guanosine phosphodiesterase, as well as anxiolytic agents at a dosage level of from about 12 to about 100 mg/kg per day ip in one dose or in up to 4 divided doses; as inhibitors or platelet aggregation in vitro and therefore of potential use in the treatment of thrombosis.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricating such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following Examples further illustrate and represent preferred embodiments of the invention. All temperatures are expressed in degrees Centigrade.

EXAMPLE 1

1-(Diethylamino)-6-[1-(diethylamino)-3-methoxy-3-oxo-1-propenyl]-5,6-dihydro-5-oxopyrazolo[1,5-c]quinazoline-2-carboxylic acid, methyl ester 1.49 g (10 mmole) of diazooxindole and 3.1 g ( 20 mmole) of $(C_2H_5)_2N-C\equiv CO_2CH_3$ (yneamine ester) in 50 ml of dry toluene is heated at reflux temperature for 24 hours. The mixture is cooled, diluted with ethyl ether and washed with dilute aqueous HCl, dilute aqueous $NaHCO_3$ and $H_2O$, dried ($CaCl_2$), treated with Darco and concentrated in vacuo. The residue is adsorbed on ca. 5 g of silica gel (slurried in $CHCl_3$ and solvent stripped in vacuo) and applied to a silica gel column (100 g, wet packed with benzene and prewashed with hexane) and eluted with $CHCl_3$/hexane (0/100 to 100/0). Fractions eluted with 0/100 to 50/50 $CHCl_3$/hexane affords a small amount (100 mg) of 3-(3-diazo-2,3-dihydro-2-oxo1H-indol-1-yl)-3-(diethylamino)-2-propenoic acid, methyl ester. Continued elution with 50/50 to 100/0 $CHCl_3$/hexane affords upon removal of solvent and crystallization of the residue from EtOAc/hexane 600 mg of the title compound (13%), m.p. 175°–177°.

This is combined with 700 mg of the title compound obtained in other reactions and recrystallized from EtOAc/hexane to give 1.0 g of the title compound, m.p. 177.5°–178.5°.

EXAMPLES 2 TO 30

Following the procedure of Example 1, but substituting the compounds indicated in Column I of Table I below for the diazooxindole and the compounds indicated in Column II below for the yneamine ester, the compounds indicated in Column III are obtained.

TABLE 1

| | Column I | | Column II | | | Column III | | |
|---|---|---|---|---|---|---|---|---|
| Ex. No. | R⁴ (position) | R⁵ (position) | $R^1$ | Z | $R_3$ | $R^4$ | $R^5$ | $R^1$ Z $R_3$ / $R^6$ |
| 2. | s-C₄H₉(5) | H | N(CH₃)₂ | —(CH₂)₂— | C₅H₁₁ | s-C₄H₉(9) | H | as per Column II / R⁶ same as R¹ |
| 3. | H | CH₃(6) | N(C₂H₅)₂ | —(CH₂)₂— | C₈H₁₇ | CH₃(7) | CH₃(8) | |
| 4. | n-C₃H₇(6) | H | NHCH₃ | —CH₂— | C₄H₉ | n-C₃H₇(8) | H | |
| 5. | CH₃(5) | CH₃(6) | N(C₂H₅)(CH₃) | —CH— / CH₃ | CH₃ | CH₃(9) | CH₃(8) | |
| 6. | C₂H₅(4) | H | N(CH₃)₂ | —CH— / CH₂CH₃ / —CH₂CH₂— | —CH₂—⟨phenyl⟩ | C₂H₅(10) | H | |
| 7. | CH₃O(4) | H | N(C₂H₅)₂ | —CH₂— / —CH₂— | C₂H₅ | CH₃O(10) | H | |
| 8. | C₂H₅O(5) | H | N(C₂H₅)₂ | —CH— / CH₃ | CH₃ | C₂H₅O(9) | H | |
| 9. | CH₃O(4) | H | N(C₂H₅)₂ | —CH₂—C(CH₃)₂—(CH₂)₂— | C₅H₁₁ | CH₃O(10) | H | |
| 10. | CH₃O(5) | OH(6) | N(C₄H₉)₂ | —CH— / CH₃ | C₂H₅ | CH₃O(9) | OH(8) | |
| 11. | H | OCH₃(7) | N(C₂H₅)₂ | —(CH₂)₂— | C₂H₅ | OH(9) | OCH₃(7) | |
| 12. | OH(5) | H | N(C₂H₅)₂ | —(CH₃)₃— / —CH₂— / —C— / CH₃ | CH₂—⟨4-methylphenyl⟩ | OH(9) | H | |
| 13. | CH₃O(5) | H | N(CH₃)₂ | —CH₂— | CH₃ | CH₃O(9) | H | |
| 14. | ⟨benzyl⟩CH₂—O—(5) | H | N(C₂H₅)₂ | —CH₂— | C₂H₅ | CH₂—⟨phenyl⟩ / CH₂O(9) | H | |
| 15. | Br(5) | H | NHCH₃ | —CH—(CH₂)₂— | C₆H₁₃ | Br(9) | H | |
| 16. | Cl(4) | CH₃(7) | NHC₃H₇ | —CH— / C₂H₅ | CH₂—⟨phenyl⟩ | Cl(10) | CH₃(7) | |
| 17. | Cl(6) | H | NHCH₃ | —(CH₂)₂— | C₄H₉ | Cl(8) | H | |
| 18. | CF₃(7) | H | N(CH₃)₂ | —CH₂— | CH₃ | CF₃(7) | H | |
| 19. | CF₃(5) | CF₃(6) | N(CH₃)₂ | —CH₂—CH— | CH₃ | CF₃(9) | CF₃(8) | |

What is claimed is:
1. Compounds of the structure

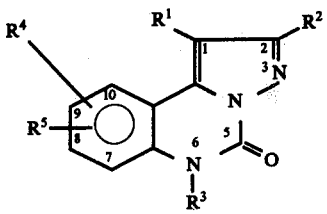

wherein
$R^1$ is alkylamino, dialkylamino, or

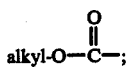

$R^2$ is alkylamino, dialkylamino, or

the alkyl moiety in the above $R^1$ and $R^2$ groups having from 1 to 8 carbons;
$R^3$ is hydrogen, lower alkyl, benzyl, phenyl or phenyl substituted by a single $R^8$ radical,

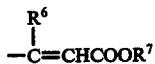

(wherein $R^6$ is amino, alkylamino having 1 to 4 carbons, or dialkylamino having 1 to 4 carbons in each alkyl, and $R^7$ is alkyl of 1 to 4 carbons), with the proviso that at least one of $R^1$ or $R^2$ is alkylamino or dialkylamino; p1 $R^4$, $R^5$ and $R^8$ may be the same or different and are hydrogen, lower alkyl of 1 to 4 carbons, lower alkoxy of 1 to 4 carbons, hydroxy, alkanoyloxy of 2 to 5 carbons,

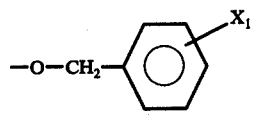

(wherein $X_1$ is hydrogen, lower alkoxy of 1 to 4 carbons), hydroxy, Cl, F, Br, $CF_3$ or $NO_2$, and physiologically acceptable salts thereof.

2. The compound of claim 1 wherein $R^1$ or $R^2$ is alkylamino.

3. The compound of claim 1 wherein $R^1$ or $R^2$ is dialkylamino.

4. The compound of claim 1 wherein $R^1$ is alkylamino.

5. The compound of claim 1 wherein $R^1$ is dialkylamino.

6. The compound of claim 1 wherein $R^1$ or $R^2$ is

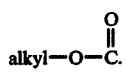

7. The compound of claim 1 wherein $R^2$ is

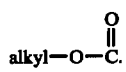

8. The compound of claim 1 wherein $R^3$ is hydrogen, lower alkyl, benzyl or phenyl and $R^1$ or $R^2$ is alkylamino or dialkylamino.

9. The compound of claim 1 wherein $R^3$ is

wherein $R^6$ is amino, alkylamino or dialkylamino and $R^7$ is alkyl.

10. The compound of claim 1 wherein $R^3$, $R^4$ and $R_5$ are hydrogen.

11. The compound of claim 1 having the name 1-(diethylamino)-6-[1-(diethylamino)-3-methoxy-3-oxo-1-propenyl]-5,6-dihydro-5-oxo-pyrazolo[1,5-c]quinazoline-2-carboxylic acid, methyl ester.

12. A pharmaceutical composition for use in treating allergic conditions comprising a therapeutic amount of a compound as defined in claim 1 and a pharmaceutically acceptable carrier therefor.

13. A method for treating allergic conditions in mammals, which comprises administering to the mammalian host a therapeutic amount of a compound as defined in claim 1.

* * * * *

UNITED STATES PATENT OFFICE
CERTIFICATE OF CORRECTION

Patent No. 4,110,452                    Dated August 29, 1978

Inventor(s) George C. Rovnyak et al.

It is certified that error appears in the above-identified patent and that said Letters Patent are hereby corrected as shown below:

In the Abstract, after the last sentence, insert --The above compounds are useful as anti-allergy and antiinflammatory agents.--
Column 2, line 36, after "alkyl)" insert --(Ia)--.
Column 3, line 38, "temperaturedependent" should read --temperature-dependent--.
Column 4, line 26, "appropriatelysubstituted" should read --appropriately-substituted--.
Column 6, line 11, "4-" should read -- 4-12 --.
Column 8, line 44, after "orally," insert --or--.
Column 9, line 29, "lubricating" should read --lubricant--.
Example 18, Column II, under "Z", "-CH-" should read -- $-CH_2-$ --.

Table 1, after Ex. 19, insert the following examples:

-- TABLE I (continued)

| | Column I | | Column II | | |
|---|---|---|---|---|---|
| Ex. No. | $R^4$ (position) | $R^5$ (position) | $R^1$ | Z | $R_3$ |
| 20. | F(5) | H | $N(CH_3)_2$ | $-CH_2-$ | $CH_3$ |
| 21. | H | H | $N(CH_3)_2$ | $-CH_2-CH(C_2H_5)-CH_2-$ | H |
| 22. | H | H | $N(CH_3)(C_2H_5)$ | $-(CH_2)_3-$ | H |
| 23. | H | H | $N(CH_3)_2$ | -- | $CH_3$ |

Column I structure: bicyclic compound with $R^4$, $R^5$ substituents, O in ring, N-H, with =$N_2$ and =O groups.

Column II formula: $R^1-C\equiv C-Z-COR_3$ (with C=O)

UNITED STATES PATENT OFFICE
CERTIFICATE OF CORRECTION

Patent No. 4,110,452                    Dated August 29, 1978

Inventor(s) George C. Rovnyak et al.

It is certified that error appears in the above-identified patent and that said Letters Patent are hereby corrected as shown below:

TABLE I (continued)

Column III

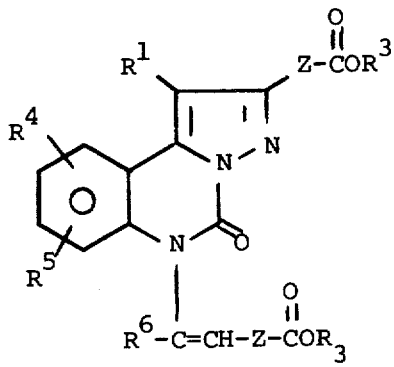

| Ex. No. | $R^4$ | $R^5$ | $R^1$  $Z$  $R_3$ | $R^6$ |
|---|---|---|---|---|
| 20. | F(9) | H | as per Column II | same as $R^1$ |
| 21. | H | H | | |
| 22. | H | H | | |
| 23. | H | H | | |

UNITED STATES PATENT OFFICE
CERTIFICATE OF CORRECTION

Patent No. 4,110,452      Dated August 29, 1978

Inventor(s) George C. Rovnyak et al.

It is certified that error appears in the above-identified patent and that said Letters Patent are hereby corrected as shown below:

TABLE I (continued)

| | Column I | | Column II | | |
|---|---|---|---|---|---|
| Ex. No. | $R^4$ (position) | $R^5$ (position) | $R^1$ | Z | $R_3$ |
| 24. | H | H | $NHCH_3$ | – | H |
| 25. | $CH_3\overset{O}{\overset{\|}{C}}O(4)$ | H | $NHC_2H_5$ | – | $C_2H_5$ |
| 26. | $CH_3(4)$ | $CH_3O(5)$ | $NHC_3H_7$ | – | H |
| 27. | $C_2H_5(5)$ | $C_2H_5(6)$ | $N(C_2H_5)_2$ | – | $CH_3$ |
| 28. | $CH_3O(4)$ | H | $N(n-C_3H_7)_2$ | – | $CH_3$ |
| 29. | $CH_3O(4)$ | H | $NHC_4H_9$ | – | $C_2H_5$ |
| 30. | $CH_3O(4)$ | H | $N(CH_3)_2$ | – | $n-C_3H_7$ |

UNITED STATES PATENT OFFICE
CERTIFICATE OF CORRECTION

Patent No. 4,110,452            Dated August 29, 1978

Inventor(s) George C. Rovnyak et al.

It is certified that error appears in the above-identified patent and that said Letters Patent are hereby corrected as shown below:

TABLE I (continued)

| Ex. No. | $R^4$ | $R^5$ | Column III $R^1$   Z   $R_3$ | $R^6$ |
|---|---|---|---|---|
| 24. | H | H | as per Column II | same as $R^1$ |
| 25. | $CH_3\overset{O}{\underset{\|\|}{C}}(10)$ | H | | |
| 26. | $CH_3(10)$ | $CH_3O(9)$ | | |
| 27. | $C_2H_5(9)$ | $C_2H_5(8)$ | | |
| 28. | $CH_3O(10)$ | H | | |
| 29. | $CH_3O(10)$ | H | | |
| 30. | $CH_3O(10)$ | H | | |

Column 13, line 38, before "$R^4$" delete "pl".

Column 14, line 34, "$R_5$" should read --$R^5$--.

Signed and Sealed this

Twenty-fourth Day of April 1979

[SEAL]

Attest:

RUTH C. MASON
*Attesting Officer*

DONALD W. BANNER
*Commissioner of Patents and Trademarks*